(12) United States Patent
Bashir et al.

(10) Patent No.: US 9,718,758 B2
(45) Date of Patent: Aug. 1, 2017

(54) METHOD FOR PURIFYING DIOCTYL PHTHALATE

(71) Applicant: SABIC BASIC INDUSTRIES CORPORATION, Riyadh (SA)

(72) Inventors: Mubarik Ali Bashir, Riyadh (SA); Mohammad Rafi, Riyadh (SA); Emmanuel Osei-Twun, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/892,728

(22) PCT Filed: Jun. 4, 2014

(86) PCT No.: PCT/IB2014/061953
§ 371 (c)(1),
(2) Date: Nov. 20, 2015

(87) PCT Pub. No.: WO2014/195887
PCT Pub. Date: Dec. 11, 2014

(65) Prior Publication Data
US 2016/0096798 A1    Apr. 7, 2016

Related U.S. Application Data

(60) Provisional application No. 61/832,576, filed on Jun. 7, 2013.

(51) Int. Cl.
| C07C 67/48 | (2006.01) |
| C07C 67/56 | (2006.01) |
| C07C 69/80 | (2006.01) |
| C08K 5/12  | (2006.01) |

(52) U.S. Cl.
CPC .............. *C07C 67/56* (2013.01); *C07C 69/80* (2013.01); *C08K 5/12* (2013.01)

(58) Field of Classification Search
CPC ........... C07C 67/56; C07C 69/80; C08K 5/12; H04W 4/06; H04W 52/241; H04W 52/245; H04W 52/383; H04W 76/043
See application file for complete search history.

(56) References Cited

U.S. PATENT DOCUMENTS

| 2,748,159 A | 5/1956 | Finelli |
| 2,862,958 A | 12/1958 | Goreau |
| 3,459,736 A | 8/1969 | Dalibor |
| 5,880,310 A | 3/1999 | Ageishi et al. |
| 2002/0104574 A1* | 8/2002 | Redler .................. A61L 29/085 138/137 |

FOREIGN PATENT DOCUMENTS

| CN | 1835908 A | 9/2006 |
| CN | 1884249 A | 12/2006 |
| CN | 101530780 | * 9/2009 |
| CN | 101530780 A | 9/2009 |
| GB | 783463 | 9/1957 |
| GB | 813867 | 5/1959 |
| GB | 1058242 | 2/1967 |
| JP | 62267341 A | 11/1987 |
| JP | 09263566 A | 10/1997 |
| JP | 2005320302 A | 11/2005 |
| WO | 2005021482 A1 | 3/2005 |
| WO | WO2005021482 | * 3/2005 |

OTHER PUBLICATIONS 780 translated, Sep. 2009.*
Habib, Rowshanul and Karim, M. Rezaul, "Antimicrobial and Cytotoxic Activity of Di-(2-ethylhexyl) Phthalate and Anhydrosophoradiol-3-acetate Isolated from *Calotropis gigantea* (Linn.) Flower", Mycobiology Mar. 2009;37(1): 31-36.
International Search Report of the International Searching Authority for PCT/IB2014/061953 mailed Sep. 24, 2014, 5 pages.
Sastry, V.M.V.S. and Rao, G.R.K., "Dioctyl phthalate, and antibacterial compound from the marine brown alga—*Sargassum wightii*", Journal of Applied Phycology, 7: 185-186 (1995).
Torane, Rasika C., et al., "Isolation and Characterisation of 1, 2 Benzenedicarboxylic acid, bis (2 ethylhexyl) ester-Dioctyl Phthalate, a Bioactive Compound from Ehretia laevis", Journal of Pharm. Research (2012) 5(6), 3251-3252.
Unknown Author, "Dioctyl Phthtalate", XP-002728241, Jun. 3, 2013, retrieved from the Internet: UURL: https://chemicalland21.com/industrialchem/plasticizer/DOP.htm, 3 pages.
Written Opinion of the International Searching Authority for PCT/IB2014/061953 mailed Sep. 24, 2014, 9 pages.
Xu, Leilei, et al., "Carbon dioxide reforming of methane over ordered mesoporous NiO—MgO—Al2O3 composite oxides", Applied Catalysis B: Environmental 108-109 (2011) p. 177-190.
International Preliminary Report on Patentability, PCT/IB2014/061953, Issued Dec. 17, 2015.
ISR/WO Mailed Sep. 24, 2014.

* cited by examiner

Primary Examiner — Yevegeny Valenrod
Assistant Examiner — Blaine G Doletski
(74) Attorney, Agent, or Firm — Cantor Colburn LLP

(57) ABSTRACT

Disclosed is a method of reducing the ultraviolet-light absorbing properties of a composition comprising dioctyl phthalate, the method comprising (a) obtaining a composition comprising dioctyl phthalate and phthalide, wherein said composition has an absorbance of greater than 0.1 at a wavelength of about from 230 to 360 nm, (b) contacting the composition with activated carbon, silica gel, or diatomaceous earth, for a sufficient amount of time to allow the phthalide to contact the activated carbon, silica gel, or diatomaceous earth, and (c) removing the composition from the activated carbon, silica gel, or diatomaceous earth, wherein the composition obtained from step (c) has an absorbance equal to or less than about 0.1 at a wavelength of about from 230 to 360 nm and has a reduced amount of phthalide when compared with the composition from step (a).

33 Claims, 2 Drawing Sheets

METHOD FOR PURIFYING DIOCTYL PHTHALATE

This application is a national stage application of PCT/IB2014/061953 filed Jun. 4, 2014, which claims priority to United States Provisional Application Serial Number 61/832,576filed Jun. 7, 2013, which are hereby incorporated by reference in their entirety.

BACKGROUND OF THE INVENTION

The invention generally concerns a process for removing phthalide from a composition that includes diisooctyl phthalate and phthalide. In particular aspects, the phthalide can be removed by contacting the composition with activated carbon or a silica containing material such as silica gel or diatomaceous earth, or any combination thereof.

Diisooctyl phthalate (DOP), also referred to as di-2-ethylhexyl phthalate (DEHP), is a commonly used plasticizer from the phthalate ester family and has been in use in flexible polyvinyl chloride (PVC) products for at least 60 years. These flexible PVC products are used in a wide range of applications and materials found in buildings, automotive parts, medical devices or equipment, and packaging applications.

Plastics used in medical devices are oftentimes sterilized with ultraviolet (UV) radiation (wavelength of about 100 to 400 nm). Such radiation can degrade the plastic and ultimately lead to plastic failure. This can be exacerbated if the plastic is efficient at absorbing UV radiation, as such absorption can result in the loss of the physical and chemical properties of the plastic. The international standard ISO 3826-1:2003 for Plastics Collapsible Containers for Human Blood and Blood Components states that the maximum permissible absorbance value of a plastic container having a capacity of less than 100 ml is 0.25 in the range of 230 nm to 360 nm. For containers greater than 100 ml, the maximum absorbance value is 0.2 for the same wavelength range. The current options available for meeting these standards are to use ingredients in the plastic that either have low absorption properties within the 230 nm to 360 nm range or to limit the amount of ingredients that may absorb within this range.

While DOP is a well-known plasticizer, the currently available commercial sources of DOP fail to meet international standards relating to the absorption properties of this plasticizer for use in medical equipment and medical devices. Further, the vast majority of processes known to purify DOP are not even concerned with UV absorption—rather, such processes relate to decolorizing DOP so that it can be optically clear and not affect the color of the resulting plastic product.

SUMMARY OF THE INVENTION

A solution to this problem has been discovered. In particular, it has been discovered that phthalide, which can be present in DOP products, can lead to increased UV absorbance of the DOP product. It was also discovered that activated charcoal or a silica containing material (e.g., silica gel or diatomaceous earth), or any combination thereof, can be used to efficiently remove phthalide from DOP, reduce the UV radiation absorbance of DOP, and result in a plasticizer that can be safely used in medical equipment/devices.

In some aspects, there is disclosed a method of reducing the ultraviolet-light absorbing properties of a composition comprising dioctyl phthalate. In other aspects, there is disclosed a method of reducing the amount of phthalide in a composition comprising dioctyl phthalate. A further aspect includes a method of making a plasticizer that meets international ISO standards for plasticizers used in medical equipment or for the actual medical equipment (e.g., 3826-1:2003(E)). The methods can include (a) obtaining a composition comprising dioctyl phthalate and phthalide, wherein said composition has an absorbance of greater than 0.1 at a wavelength of about from 230 to 360 nm (b) contacting the composition with activated carbon or a silica containing material (e.g., silica gel or diatomaceous earth) for a sufficient amount of time to allow the phthalide to contact the activated carbon or the silica containing material (e.g., more than 25, 30, 35, 40, 45, 50, 55, or 60 minutes or more), and (c) removing the composition from the activated carbon or the silica containing material, wherein the composition obtained from step (c) has an absorbance equal to or less than about 0.1 at a wavelength of about from 230 to 360 nm and/or has a reduced amount of phthalide when compared with the composition from step (a). The composition from step (a) can have an absorbance value greater than 0.1 at a wavelength of about 230 nm and the composition obtained from step (c) can have an absorbance equal to or less than about 0.1 at a wavelength of about 230 nm. The composition from step (a) can have an absorbance of from about 0.35 to about 0.40 at a wavelength of 230 nanometers. The absorbance value at a wavelength of about 230 nm for the composition at step (a) can be reduced by a factor of at least 1 after performing the contacting step (b) and the removing step (c). The method can result in at least 50, 60, 70, 80, or 90% of the phthalide being removed from the composition from step (a) after performing the contacting step (b) and the removing step (c). In particular aspects, at least 80 or 90% of the phthalide can be removed. In some aspects, the composition from step (a) is in liquid form and the activated carbon or silica containing material is in solid form (e.g., particulate, granulated, beaded, powdered, etc.). The method can be performed such that the mobile phase is the composition from step (a) and the stationary phase is the activated charcoal or silica containing material, and the mobile phase is passed over or through the stationary phase or the mobile phase is mixed with the stationary phase. In certain aspects, column chromatography can be used. In some embodiments, the activated carbon or silica containing material can absorb or bind to the phthalide so as to remove it from the DOP composition provided that the phthalide contacts the activated carbon or silica containing material for a sufficient period of time to allow for the phthalide to be absorbed by or bind to the activated carbon or silica containing material. In some aspects, the activated carbon or silica containing material can be included in a second composition. Further, it is contemplated that a combination of activated carbon and/or silica containing material (e.g., activated carbon and silica gel, activated carbon and diatomaceous earth, silica gel and diatomaceous earth, or activated carbon, silica gel, and diatomaceous earth) can be used to remove the phthalide from the DOP composition. The method can also include a further step (d) such as isolating, purifying, or extracting the composition obtained from step (c). Such isolation, purifying, or extracting step can include further removing dioctyl phthalate from the composition obtained from step (c). The isolating or purifying or extracting step can be performed with the use of an anti-solvent (e.g., water). In some instances, no further processing steps are performed after steps (c) or (d) in that no further purification/isolation/extraction is performed. The composition obtained from step (c) can be used as a plasticizer in an article of manufacture. The article of manufacture can be a plastic container or tubing. The article of manufacture can be a medical equipment or a medical device or a plastic piece or material that is part of or forms part of the medical equipment or medical device (e.g., intravenous tubing and bags, catheters, nasogastric tubes, dialysis bags and tubing, blood bags and transfusion tubing, air tubes, etc.). In certain aspects, the composition obtained from step (c) meets international ISO standards for UV absorption properties of plasticizers used in medical equipment or medical devices or the UV absorption properties of the actual medical equipment or medical device (e.g., ISO 3826-1:2003(E)). In some aspects, the composition from step (a) can include at least 100, 200, 300, 400, or 1000 parts per million or comprises at least 0.01, 0.02, 0.03, 0.04, or 0.1% by weight, or more of phthalide, or from 100 to 1000 parts per million or from 0.01 to 0.1% by weight of phthalide. In certain aspects, the composition from step (a) can include 100 to 600 parts per million or comprises 0.01 to 0.06% by weight of phthalide. In even further aspects, the composition from step (a) can include 300 to 600 parts per million or comprises 0.03 to 0.06% by weight of phthalide.

In another embodiment there is a composition comprising dioctyl phthalate that was produced by any one of the methods discussed above or throughout the specification. Further, there is also disclosed a plasticizer produced by any one of the methods discussed above or throughout the specification.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Diisooctyl phthalate (DOP) has been used as a plasticizer in medical devices ranging from intravenous tubing and bags, catheters, nasogastric tubes, dialysis bags, tubing, blood bags, transfusion tubing, and air tubes. The reason for this is that DOP works well as a plasticizer. As discussed above, however, one of the problems with this plasticizer is that the currently available commercial products have a relatively high ultraviolet light absorption capacity. Couple this with the fact that ultraviolet radiation is commonly used to sterilize the aforementioned medical devices, the life span of the medical devices can be substantially shortened—the plastic material absorbs the ultraviolet light radiation, thereby damaging the physical and chemical properties of the plastic. Failure of plastics in medical devices presents a significant problem from the supplier's perspective as well as from the patient's perspective.

The inventors have discovered a solution to the current problem associated with DOP containing compositions for use as plasticizers. The solution provides a cost and time efficient process to reduce the ultraviolet light absorbing properties of DOP. In particular, the solution resides in the use of activated carbon or silica containing materials (e.g., silica gel or diatomaceous earth), or any combination thereof, to quickly and efficiently remove phthalide from DOP. This process can be used to make the DOP plasticizer product sufficient for use in medical device applications.

These and other non-limiting aspects are discussed in further detail in the following sections.

A. Composition Containing DOP and Phthalide

Diisooctyl phthalate (DOP) is a diester of phthalic acid. It is a viscous colorless liquid soluble in organic solvents and insoluble in water. As discussed above, it has excellent plasticizing properties and is typically used as plasticizer for polyvinyl chloride. There are several acronyms for DOP such as di-2-ethyl hexyl phthalate (DEHP), bis(2-ethylhexyl) phthalate, dioctylphthalate etc. Its chemical structure is:

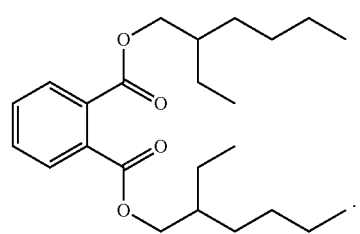 [SMILES: CCCCC(CC)COC(=O)c1ccccc1C(=O)OCC(CC)CCCC]

DOP can be manufactured by esterification of 2-ethylhexanol and phthalic anhydride under moderate conditions. The problem with this process in the context of the present invention is that phthalide can be present in phthalic anhydride. Phthalide has the following structure:

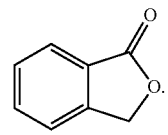

Figure 1:
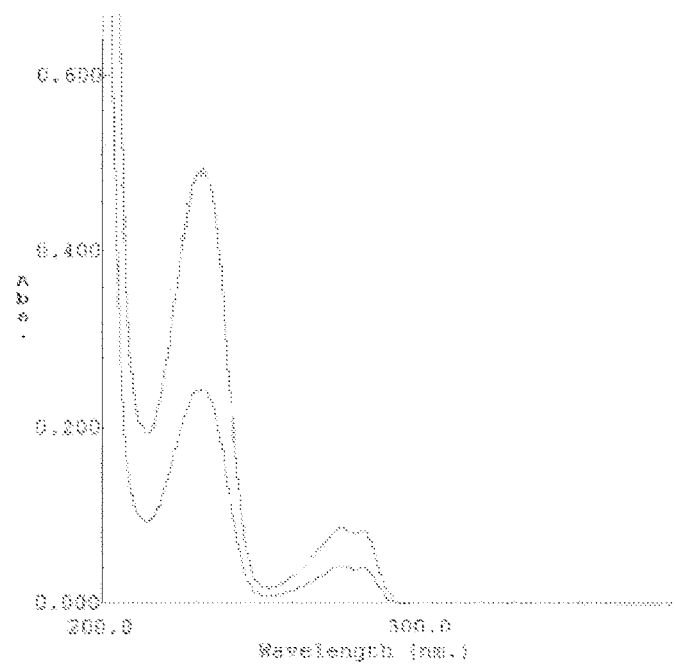
FIG. 1: UV-Vis spectra showing absorbance for pure phthalide at two different concentrations in the presence of water.

One possible reason for the presence of phthalide is that phthalic anhydride is typically prepared by oxidation of o-xylene, which is first converted to o-tolualdehyde and then to both phthalic anhydride and phthalide. While the majority of phthalide is then converted to phthalic anhydride, some of the phthalide remains and is introduced into compositions that include DOP. The absorbance maximum wavelength for phthalide is about 230 nm (see FIG. 1), thereby making it relatively efficient at absorbing UV radiation. Removal of phthalides from DOP compositions/products can result in a plasticizer that is better suited for medical equipment and device applications.

B. Activated Carbon/Silica Containing Material

The materials that can be used to separate phthalide from a composition comprising DOP and phthalide include activated carbon and silica containing material such as silica gel or diatomaceous earth. Without wishing to be bound by theory, it is believed that the when DOP/phthalide containing composition is contacted with the activated carbon and/or silica containing material for a sufficient period of time, the phthalide is adsorbed by or binds to the activated carbon and/or silica containing material. Then when the composition is removed from the activated carbon and/or silica containing material, the phthalide remains behind and bound to the activated carbon and/or silica containing material. This results in a DOP containing composition that has a reduced amount of phthalide and therefore a reduced ability to absorb UV radiation, thereby making it useful as a plasticizer in medical equipment and device applications.

Each of activated carbon and silica containing materials are commercially available from a wide range of companies. For instance, Sigma-Aldrich® Co. LLC (St. Louis, Miss., USA) provides a good selection of various types of activated carbon, silica gel, and diatomaceous earth products that can be used in the context of the present invention.

With respect to activated carbon (or active carbon), it is a form of carbon that has been processed to be riddled with small, low-volume pores that increase the surface area available for adsorption or chemical reactions. Oxygen or other gases can be used as the processing agent for creating the pores. It can be further processed or modified to have additional reactive groups on its surface. There are several classes of activated carbon that can be used in the context of the present invention. For instance, powdered activated carbon (PAC) is in particulate form as powders or fine granules typically less than 1.0 mm in size with an average diameter between 0.15 and 0.25 mm. Granular activated carbon (GAC), by comparison, typically has a relatively larger particle size compared to powdered activated carbon and consequently, presents a smaller external surface. GAC can be either in granular or extruded form. GAC is designated by sizes such as 8×20, 20×40, or 8×30 for liquid phase applications and 4×6, 4×8 or 4×10 for vapor phase applications. By way of example, a 20×40 carbon is made of particles that will pass through a U.S. Standard Mesh Size No. 20 sieve (0.84 mm) (generally specified as 85% passing) but be retained on a U.S. Standard Mesh Size No. 40 sieve (0.42 mm) (generally specified as 95% retained). Extruded activated carbon (EAC) combines powdered activated carbon with a binder. The activated carbon and binder can be fused together and extruded into a desired shape (e.g., cylindrical shaped activated carbon block with diameters from 0.8 to 130 mm are typical). Beaded activated carbon (BAC) is typically made from petroleum pitch and supplied in diameters from approximately 0.35 to 0.80 mm. Impregnated carbon is porous carbons containing an inorganic impregnate such as iodine, silver, a cation (e.g., Al, Mn, Zn, Fe, Li, Ca, etc.).

Turning to silica gel, it is a porous form of silicon dioxide ($SiO_2$). It can be processed into granular or beaded form. The surface of the silica particles can be modified to have additional reactive groups. The particle size range of silica gel particles is typically between about 10 to 1000 microns or 10 to 500 microns or 35 to 300 microns.

With respect to diatomaceous earth, it is a naturally occurring siliceous sedimentary rock. It typically has a particle size ranging from 1, 5, 10, 15, 20, 25, or more microns to more than 1 mm, or more typically between 10 to 200 microns. It generally comes in powdered or granulated form and takes on a white to white-grey/pink appearance (see, e.g., Sigma-Aldrich® products). The majority of diatomaceous earth is silica (at least about 85 or at least about 90% by weight is silica).

C. Contacting and Removal Steps

As shown in the examples, the contacting step can be a simple mixture and stirring of the DOP/phthalide composition with the activated carbon or silica containing material followed by removal of the composition from the material. The examples also show that the contacting step can be more typical column chromatography set-up, with the mobile phase being the DOP/phthalide composition and the stationary phase being the activated carbon or silica containing material. In either instance, the contacting step should be for a sufficient period of time to ensure adsorption of phthalide by the activated carbon or silica containing material.

The removal step can be performed by simple filtration or separation of the DOP/phthalide composition from the activated carbon or silica containing material, where the resulting composition has a reduced amount of phthalide. Once separated, further processing and purification steps are not required by be performed on the composition, if desired. As discussed throughout, the resulting DOP composition can be used as a plasticizer in a variety of plastics. Notably, it can be used in medical device/medical equipment applications and can meet the UV absorbance international standards for such devices/equipment.

Current products on the market do not meet these standards or require a multitude of processing steps, thereby increasing the costs associated with making such a plasticizer for medical devices and equipment applications.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Activated Charcoal

This example provides data confirming that the process of the present invention can be used to remove phthalide from a diisooctyphthalate (DOP) sample. The experimental set-up included using a glass column for treating diisooctyphthalate (DOP) on activated charcoal (DOP obtained from SABIC (Saudi Arabia). A known weight of the activated charcoal is taken and DOP equivalent to one bed volume is passed and, for the purposes of ultraviolet light analysis, the resulting DOP sample is extracted with water (1:10 w/w) at 120° C. for 20 min and the aqueous portion is separated and scanned using 1 cm cells in the range 600-200 nm.

Figure 2:
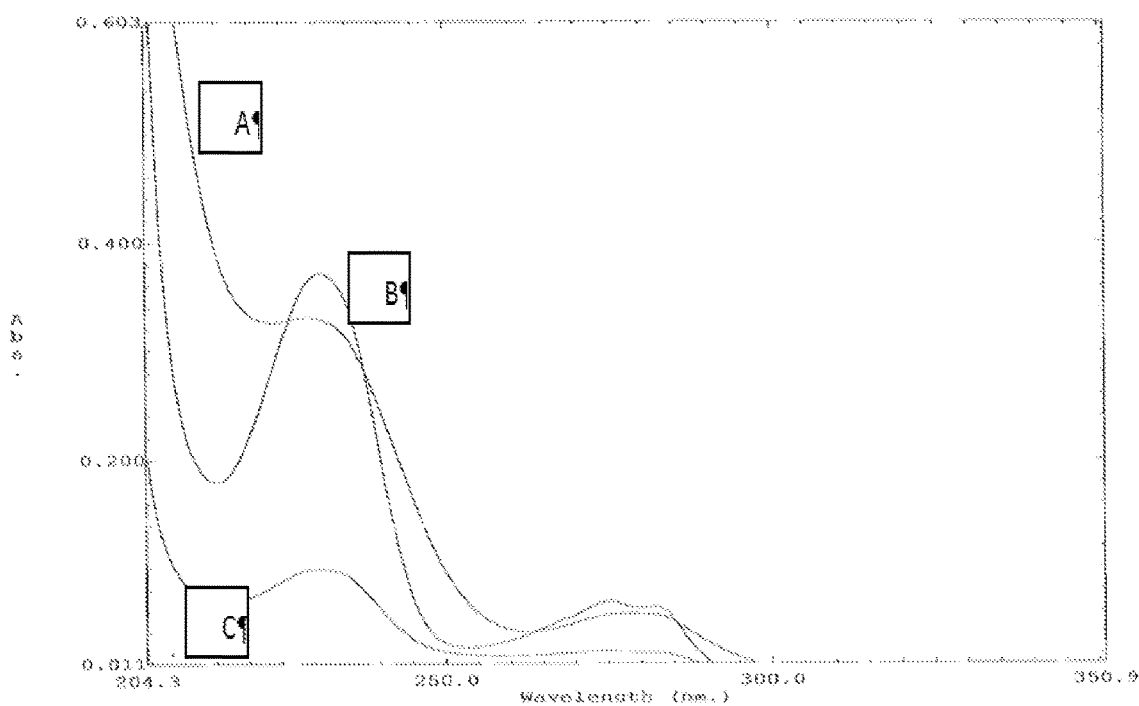
FIG. 2(A)-(C): UV-Vis spectra showing absorbance of diluted phthalide (A), untreated DOP (B), and treated DOP (C).

Experiments were performed by taking about 55 g of activated charcoal occupying about 85 ml volume in a glass cylinder of about 50 mm internal diameter. The Activated charcoal was bead-shaped activated carbon (BAC) from Kureha Chemical Industry (Japan), with an MP grade and average particle size of 0.5±0.05 mm. The flow rate ranged from 2-4 ml/min. Fractions were collected in terms of bed volumes and the UV absorbance of the aqueous extract at three wavelengths were measured (Table 1). FIGS. 2A-C includes three spectral scans: (A) is control which included diluted phthalide; (B) is the DOP sample prior to treatment; and (C) is DOP sample after treatment. FIGS. 2A-C confirm that absorbance at 230 nm for the treated DOP is substantially lower than the pre-treated DOP. Also, the absorbance at 230 nm for the treated DOP is below 0.1, and the absorbance between 230 to 360 nm is below 0.2, thereby meeting the UV absorbance standards for ISO 3826-1:2003 (E).

TABLE 1

| Bed Volume | at 230 nm | at 275 nm | at 284 nm |
|---|---|---|---|
| 1 | 0.0247 | 0.0092 | 0.0084 |
| 2 | 0.0291 | 0.0085 | 0.0081 |
| 3 | 0.0555 | 0.0135 | 0.0123 |
| 4 | 0.0621 | 0.0144 | 0.0129 |
| 5 | 0.0682 | 0.0159 | 0.0144 |
| 6 | 0.0533 | 0.0114 | 0.0099 |
| 7 | 0.0659 | 0.0151 | 0.0133 |

Figure 3:
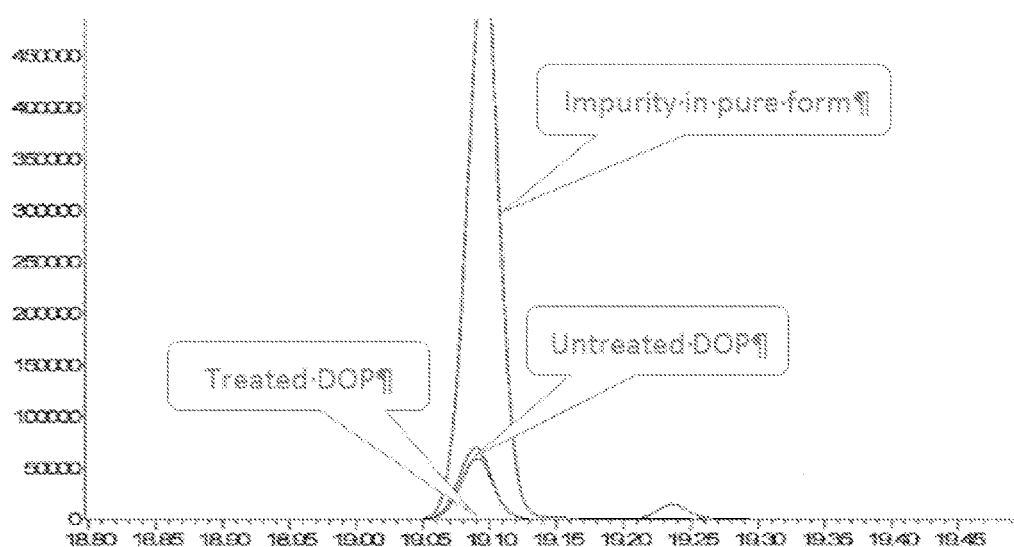
FIG. 3: GC MS chromatogram for pure phthalide ("impurity in pure form"), untreated DOP, and treated DOP.

An additional experiment using gas chromatography-mass spectrometry was carried out to confirm that the impurity responsible for the increased UV absorbance in the untreated sample of DOP was phthalide (see FIG. 3). The experimental set-up included a GC column with fused silica capillary column DB-5ms (Methylphenyl siloxane; 30 M×0.32 mm ID; 0.25 micron film thickness). The GC oven was programmed from 50° C. to 250° C. with an initial and final times of 0 and 10 minutes, respectively. 0.2 μL of sample was injected and the split ratio was set at 100:1. The carrier gas, helium, was at a flow of 1 mL/min. The GCMS instrument was AGILENT 5975C MSD coupled to a 7890A gas chromatograph. The spectrometer was operated in the SIM mode by monitoring the major ions of the compound (m/z=50.1, 51.1, 77.1, 78.1, 105.1, 106.1, 133.1, 134.1, and 135.1). The pattern of these ions was used for identification and the most intense ion (m/z=105.1) was used for quantification.

Example 2

Diatomaceous Earth

Another experiment was performed to confirm that diatomaceous earth can remove phthalide from a DOP sample. In particular, 100 g of DOP sample was heated at 120° C. 5-10 g of diatomaceous earth (MCM 48 type) was added into the sample and stirred for 1 hour at 120° C. Subsequently, the DOP sample was filtered, cooled, and subjected to the UV absorbance assay described above. Reduction of UV absorbance well below the acceptable limit (<0.1 at 230 nm) was observed.

Example 3

Silica Gel

Using the same experimental set-up as described in Example 1, a third experiment was performed to confirm that silica gel can remove phthalide from a DOP sample. In particular, one bed volume of untreated DOP passed through bed of silica gel (Silica Gel 30-70 mesh size from FISONS) in glass column. Reduction of UV absorbance well below the acceptable limit (<0.1 at 230 nm) was observed.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The wavelength-conversion materials, organic fluorescent dyes, and/or polymeric matrices of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the wavelength-conversion materials, organic fluorescent dyes, and/or polymeric matrices of the present invention are their ability to efficiently absorb light comprising a wavelength of 500 to 700 nm and emitting the absorbed light at a wavelength of greater than 550 to 800.

The invention claimed is:

1. A method of reducing the ultraviolet-light absorbing properties of a composition comprising dioctyl phthalate, the method comprising:
   (a) obtaining a composition comprising dioctyl phthalate and phthalide, wherein said composition has an absorbance of greater than 0.1 at a wavelength of about from 230 to 360 nm;
   (b) contacting the composition with an activated carbon or a silica containing material for a sufficient amount of time to allow the phthalide to contact the activated carbon or the silica containing material; and
   (c) removing the composition from the activated carbon or the silica containing material,
   wherein the composition obtained from step (c) has an absorbance equal to or less than about 0.1 at a wavelength of about from 230 to 360 nm, and has a reduced amount of phthalide when compared with the composition from step (a),
   wherein the activated carbon, when present, has an average particle size of 0.15 to 130 millimeters, and
   wherein the silica containing material, when present, is a diatomaceous earth comprising at least about 85 weight percent silica, a silica gel, or a combination thereof.

2. The method of claim 1, wherein the composition from step (a) has an absorbance greater than 0.1 at a wavelength of about 230 nm and the composition obtained from step (c) has an absorbance equal to or less than about 0.1 at a wavelength of about 230 nm.

3. The method of claim 2, wherein the composition from step (a) has an absorbance of from about 0.35 to about 0.40 at a wavelength of 230 nanometers.

4. The method of claim 1, wherein the absorbance of the composition from step (a) at a wavelength of about 230 nm is reduced by a factor of at least 1 after performing the contacting step (b) and the removing step (c).

5. The method of claim 1, wherein at least 50% of the phthalide is removed from the composition from step (a) after performing the contacting step (b) and the removing step (c).

6. The method of claim 5, wherein at least 90% of the phthalide is removed from the composition from step (a) after performing the contacting step (b) and the removing step (c).

7. The method of claim 1, wherein steps (b) and (c) are chromatography steps.

8. The method of claim 1, comprising isolating or purifying or extracting dioctyl phthalate from the composition obtained from step (c) by the addition of an anti-solvent.

9. The method of claim 8, wherein the anti-solvent is water.

10. The method of claim 1, wherein no further processing steps are performed after step (c) to remove phthalide from the composition.

11. The method of claim 1, wherein the composition is contacted with activated carbon.

12. The method of claim 1, wherein the composition is contacted with the silica containing material.

13. The method of claim 1, comprising combining the composition obtained from step (c) as a plasticizer to a composition for the manufacture of an article of manufacture.

14. The method of claim 13, wherein the article of manufacture is a container or tubing or medical device.

15. The method of claim 1, wherein the composition obtained from step (c) meets international ISO standard 3826-1:2003(E).

16. The method of claim 1, wherein the composition from step (a) comprises at least 100 parts per million of phthalide.

17. The method of claim 1, wherein the composition from step (a) comprises 100 to 600 parts per million by weight of phthalide.

18. The method of claim 17, wherein the composition from step (a) comprises 300 to 600 parts per million of phthalide.

19. A method of reducing an amount of phthalide in a composition comprising dioctyl phthalate, the method comprising:
(a) obtaining a composition comprising dioctyl phthalate and phthalide;
(b) contacting the composition with activated carbon or a silica containing material for a sufficient amount of time to allow the phthalide to contact the activated carbon or the silica containing material; and
(c) removing the composition from the activated carbon or the silica containing material,
wherein the composition obtained from step (c) has a reduced amount of phthalide when compared with the composition from step (a)
wherein the activated carbon, when present, has an average particle size of 0.15 to 130 millimeters, and
wherein the silica containing material, when present, is a diatomaceous earth comprising at least about 85 weight percent silica, a silica gel, or a combination thereof.

20. The method of claim 19, wherein at least 50% of the phthalide is removed from the composition from step (a) after performing the contacting step (b) and the removing step (c).

21. The method of claim 20, wherein at least 90% of the phthalide is removed from the composition from step (a) after performing the contacting step (b) and the removing step (c).

22. The method of claim 19, wherein the composition from step (a) comprises at least 100 parts per million of phthalide.

23. The method of claim 19, wherein the composition from step (a) comprises 100 to 600 parts per million of phthalide.

24. The method of claim 23, wherein the composition from step (a) comprises 300 to 600 parts per million of phthalide.

25. A method of making a plasticizer that meets international ISO standard 3826-1:2003(E), the method comprising:
(a) obtaining a composition comprising dioctyl phthalate and phthalide;
(b) contacting the composition with activated carbon or a silica containing material for a sufficient amount of time to allow the phthalide to contact the activated carbon or the silica containing material; and
(c) removing the composition from the activated carbon or the silica containing material to obtain the plasticizer,
wherein the plasticizer obtained from step (c) meets international ISO standard 3826-1 :2003 (E),
wherein the activated carbon, when present, has an average particle size of 0.15 to 130 millimeters, and
wherein the silica containing material, when present, is a diatomaceous earth comprising at least about 85 weight percent silica, a silica gel, or a combination thereof.

26. The method of claim 25, wherein the plasticizer obtained from step (c) has a reduced amount of phthalide when compared with the composition from step (a).

27. The method of claim 25, wherein the plasticizer obtained from step (c) has an absorbance equal to or less than about 0.1 at a wavelength of about from 230 to 360 nm.

28. The method of claim 27, wherein the plasticizer obtained from step (c) has an absorbance equal to or less than about 0.1 at a wavelength of about 230.

29. The method of claim 25, wherein at least 50% of the phthalide is removed from the composition from step (a) after performing the contacting step (b) and the removing step (c).

30. The method of claim 29, wherein at least 90% of the phthalide is removed from the composition from step (a) after performing the contacting step (b) and the removing step (c).

31. The method of claim 25, wherein the composition from step (a) comprises at least 100 parts per million of phthalide.

32. The method of claim 25, wherein the composition from step (a) comprises 100 to 600 parts per million of phthalide.

33. The method of claim 32, wherein the composition from step (a) comprises 300 to 600 parts of phthalide.

* * * * *